United States Patent
Mao

(10) Patent No.: US 9,296,774 B2
(45) Date of Patent: Mar. 29, 2016

(54) HALOGENATED DIDEOXY SUGAR DERIVATES, PREPARATION METHOD AND APPLICATION THEREOF

(75) Inventor: Hua Mao, Suzhou (CN)

(73) Assignee: Suzhou Harmony Biotechnology Co., Ltd., Suzhou (CN)

( * ) Notice: Subject to any disclaimer, the term of this patent is extended or adjusted under 35 U.S.C. 154(b) by 657 days.

(21) Appl. No.: 13/540,609

(22) Filed: Jul. 2, 2012

(65) Prior Publication Data
US 2012/0283198 A1  Nov. 8, 2012

Related U.S. Application Data

(63) Continuation-in-part of application No. PCT/CN2010/001129, filed on Jul. 26, 2010.

(30) Foreign Application Priority Data

Dec. 30, 2009 (CN) .......................... 2009 1 0247577

(51) Int. Cl.
| | |
|---|---|
| A01N 43/04 | (2006.01) |
| A61K 31/70 | (2006.01) |
| A01N 43/16 | (2006.01) |
| A61K 31/35 | (2006.01) |
| C07H 5/04 | (2006.01) |
| C07H 5/06 | (2006.01) |
| C08B 37/00 | (2006.01) |
| C07H 11/04 | (2006.01) |
| C07H 5/02 | (2006.01) |
| C07D 493/04 | (2006.01) |

(52) U.S. Cl.
CPC .............. *C07H 11/04* (2013.01); *C07D 493/04* (2013.01); *C07H 5/02* (2013.01)

(58) Field of Classification Search
CPC ............ C07H 5/02; C07H 11/04; C07H 7/00; C07D 493/04; A61K 31/7028; A61K 31/7042
USPC .......................... 514/25, 23, 27, 460; 536/18.7
See application file for complete search history.

(56) References Cited

U.S. PATENT DOCUMENTS

| 5,622,936 A | 4/1997 | Wiessler et al. |
| 6,979,675 B2 | 12/2005 | Tidmarsh |

FOREIGN PATENT DOCUMENTS

| WO | WO 2008/011588 A2 | 1/2008 |
| WO | WO 2009/143515 A2 | 11/2009 |

OTHER PUBLICATIONS

Definition of "compound" and "composition" from the Grant & Hackh's Chemical Dictionary (1987) p. 148, McGraw-Hill, Inc.*
Niggemann, J., Lindhorst, T.K., Walfort, M., Laupichler, L., Sajus, H., Thiem, J. (1993) Synthetic approaches to 2-deoxyglycosyl phosphates. Carbohydrate Research, vol. 246, p. 173-183.*

* cited by examiner

*Primary Examiner* — Scarlett Goon
(74) *Attorney, Agent, or Firm* — Manni Li; Mei & Mark LLP

(57) ABSTRACT

A halogenated dideoxy sugar derivative, having the following general structure I wherein X is halogen,

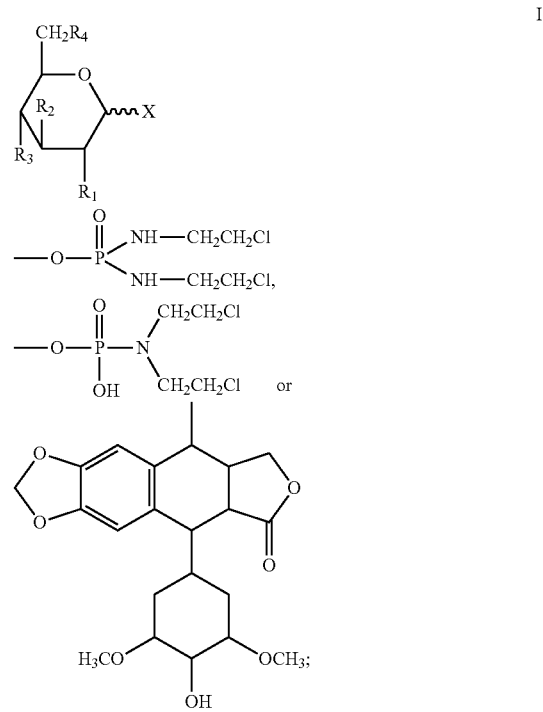

$R_1$ and $R_2$ are H or Br; $R_3$ and $R_4$ are OH or OAc. The compounds 1-14 of the current invention has strong inhibition effect on human nasopharyngeal cancer CNE-2Z cells, human lung cancer A549 cells, human colon cancer HT-29 cells, human liver cancer Bel-7402 cells, human rectum cancer cells HCE 8693, human stomach cancer BGC-803 cells, human esophagus cancer CaEs-17 cells, human breast cancer cells MCF-7, human ovarian cancer cells A2780, pancreatic cancer cells PC-3, human bladder cells EJ, human brain glia cells TG-905, human leukemia cells K562, human melanoma M 14 cells and human anaplastic thyroid carcinoma TA-K cells. They can be used to prepare anti-tumor medicament and have significant clinic value.

20 Claims, No Drawings

HALOGENATED DIDEOXY SUGAR DERIVATES, PREPARATION METHOD AND APPLICATION THEREOF

CROSS-REFERENCE TO RELATED APPLICATIONS

This application is a continuation-in-part of International Patent Application No. PCT/CN2010/001129 with an international filing date of Jul. 26, 2010, designating the United States, now pending, and further claims priority benefits to Chinese Patent Application No. 200910247577.1 filed Dec. 30, 2009. The contents of all of the aforementioned applications, including any intervening amendments thereto, are incorporated herein by reference.

BACKGROUND OF THE INVENTION

1. Field of the Invention

The current invention is related to pharmaceutical chemistry, and more particularly to a method to produce halogenated dideoxy sugar derivates as well as their applications.

2. Description of the Related Art

In the last 30 years, more and more biological functions of sugars have been revealed. Scientists have found out that sugars can boost immune system and have anti-bacteria and anti-tumor effects. One kind of sugars is named as 2-deoxy-glucose, whose structural characteristic is that the —OH on 2 position of the sugar ring is replaced by H, alkyl, amino group, and other functional groups. This kind of sugar has anti-tumor effect. In 1982, George Tidmarsh et al., U.S. Pat. No. 6,979,675 entitled "Treatment of cancer with 2-deoxy-glucose" is based on the anti-tumor effect of 2-DG (2-deoxy-gluclose). Until now, the research on deoxy sugar has been extended to multi-deoxy sugars and their derivatives. In PCT/US2009/045157, 2-halogenated-deoxyglucose and 3,4-deoxymannitose have been mentioned. However, when studying the mechanisms of the deoxy sugars, scientists have shown that pure 2-deoxyglucose does not possess very pronounced anti-tumor effect. Therefore, scientists have strived to find a deoxy sugar, which is easier to absorb and has a more potent anti-tumor effect.

The inventor of the current invention has discovered that, when acetylated and halogenated, deoxy sugars can be more easily absorbed and enter into cancer cells faster. In addition, when the hydroxyl group on its 1 position is halogenated, the halogenated deoxy sugar formed has a much stronger effect (according to normal tumor cell test), and it is also easier to product derivates. Furthermore, when combined with mustine, podophyllotoxin and other anti-tumor functional groups, the anti-tumor function of acetylated deoxy sugars can be significantly enhanced. This kind of sugars possess general anti-tumor effects, not only to common cancers, such as stomach cancer, esophagus cancer, liver cancer, bile cancer, rectum cancer, intestinal cancer, lung cancer, rhinopharyngocele, prostate cancer, nervous system cancer, breast cancer, ovarian cancer, cervis cancer, etc., but also to malignant melanoma, pancreas cancer, anaplastic thyroid carcinoma, metastatictumorofbone, leukemia and other malignant cancers. During the study of their mechanisms, it has been shown that after these compounds enter cancer cells, with various enzymes, they are first deacetylated, their glycosidic bonds are split and form deoxy sugar, and mustine, podophyllotoxin, which act on tumor cells simultaneously so that double anti-tumor functions are achieved.

SUMMARY OF THE INVENTION

The technical problem of the current invention is to overcome the drawbacks present in the current state of the art, and to remedy the structure of deoxy sugar so that it has double anti-tumor effects and a wider treatment scope and can be used to treat malignant melanoma, pancreatic cancer, anaplastic thyroid carcinoma, metastatic tumor of bone, leukemia and other highly malignant carcinomas.

The current invention provides a halogenated dideoxy sugar derivative, characterised in that the derivative has the following general structure I

wherein X is halogen,

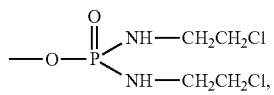

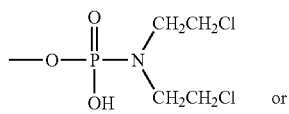

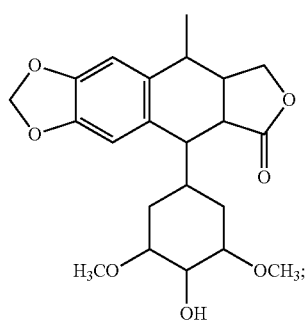 [SMILES: COC1CC(C2c3cc4c(cc3C(C)C3COC(=O)C32)OCO4)CC(OC)C1O]

$R_1$ and $R_2$ are H or Br; $R_3$ and $R_4$ are OH or OAc.

The current invention also provides compound b with the following structure.

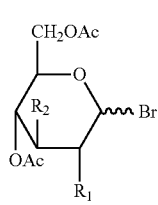

wherein $R_1$ and $R_2$ are H or Br respectively; and wherein the compound b comprises compounds 1, 2, 3, and 4 with the following structures:

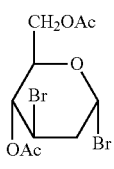  1

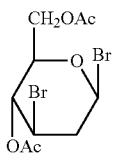  2

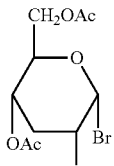  3

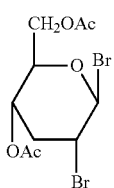  4 wherein compounds 1, 2, 3, and 4 are all white powders with the following physical characteristics:

Melting Points:

|  | compound | | | |
| --- | --- | --- | --- | --- |
|  | 1 | 2 | 3 | 4 |
| Melting point (° C.) | 84 | 79 | 88 | 82 |

Optical Rotation

|  | compound | | | |
| --- | --- | --- | --- | --- |
|  | 1 | 2 | 3 | 4 |
| Optical rotation°(CHCl$_3$) | +5 | −26 | −23 | −50 |

The current invention also provides compound c with the following structure.

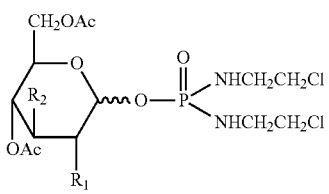  c wherein R$_1$ and R$_2$ are H or Br respectively, and wherein the compound c comprises compounds 5, 6, 7 and 8 with the following structures:

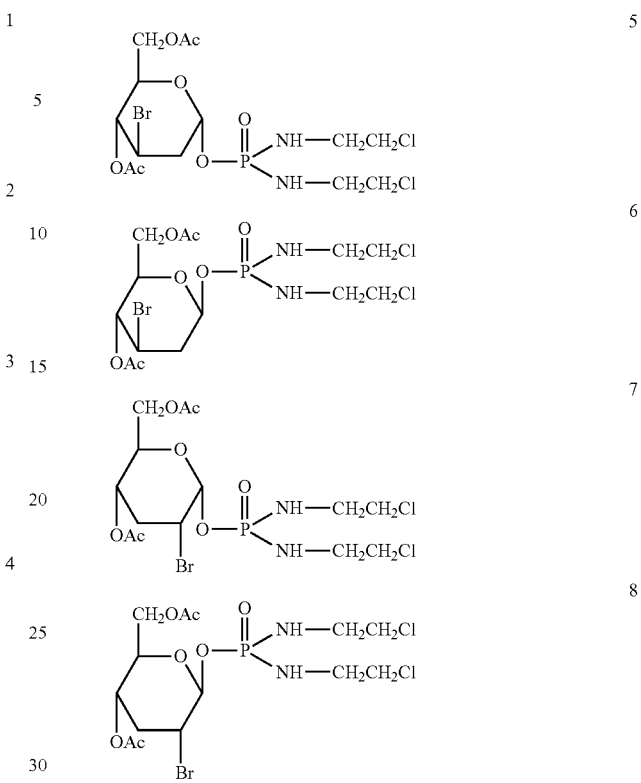

wherein compounds 5, 6, 7 and 8 are all white powders with the following physical characteristics:

Melting Points:

|  | compound | | | |
| --- | --- | --- | --- | --- |
|  | 5 | 6 | 7 | 8 |
| Melting point(° C.) | 120 | 109 | 125 | 113 |

Optical Rotation:

|  | compound | | | |
| --- | --- | --- | --- | --- |
|  | 5 | 6 | 7 | 8 |
| Optical rotation°(CHCl$_3$) | +144 | −121 | +106 | −101 |

The current invention also provides compound d with the following structure:

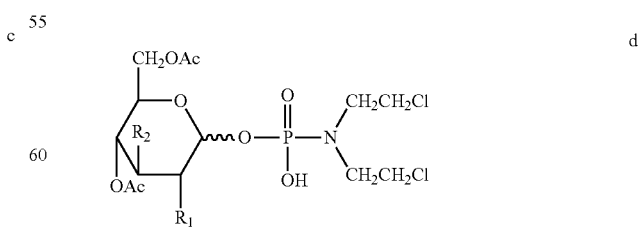  d wherein R$_1$ and R$_2$ are H or Br respectively, and wherein the compound c comprises compounds 9, 10, 11 and 12 with the following structures:

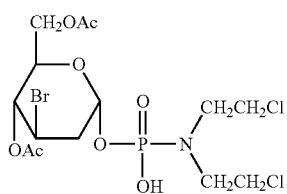

9

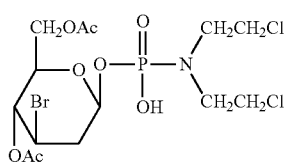

10

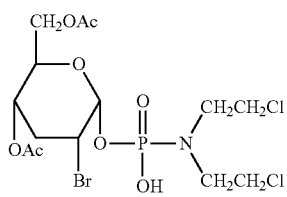

11

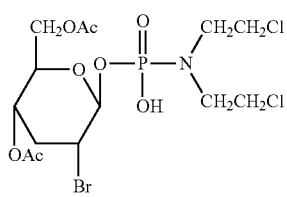

12 wherein compounds 9, 10, 11 and 12 are all white powders with the following physical characteristics:

Melting Point:

|  | compound | | | |
| --- | --- | --- | --- | --- |
|  | 9 | 10 | 11 | 12 |
| Melting point (° C.) | 117 | 105 | 118 | 108 |

Optical Rotation:

|  | compound | | | |
| --- | --- | --- | --- | --- |
|  | 9 | 10 | 11 | 12 |
| Optical rotation°(CHCl3) | +58 | −78 | −5 | −128 |

The current invention also provides compound e with the following structure:

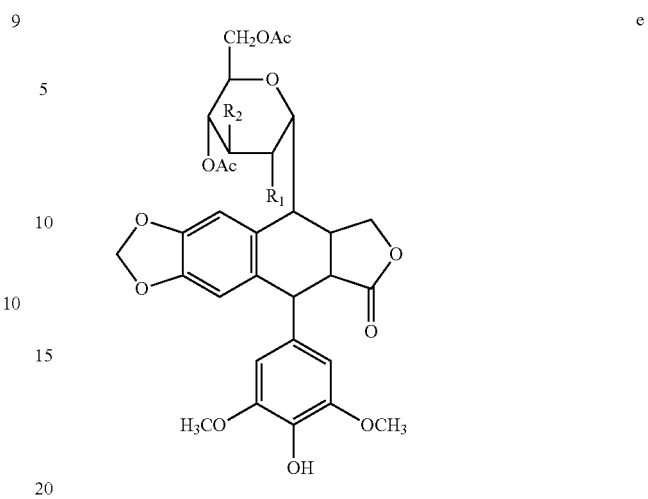

e wherein $R_1$ and $R_2$ are H or Br respectively, and wherein the compound e comprises compounds 13 and 14 with the following structures:

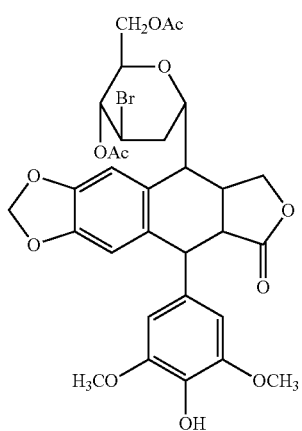

13

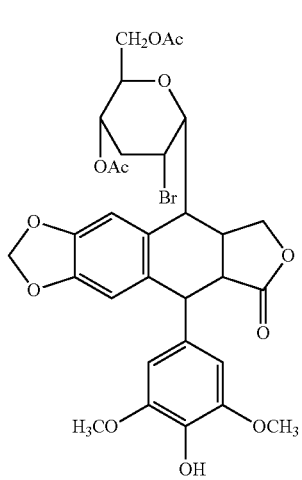

14 wherein compounds 13 and 14 are all white powders with the following physical characteristics:

Melting Points:

|  | compound | |
| --- | --- | --- |
|  | 13 | 14 |
| Melting point (° C.) | 107 | 121 |

Optical Rotation:

|  | compound | |
| --- | --- | --- |
|  | 13 | 14 |
| Optical rotation°(CHCl3) | −85 | +57 |

The other object of the current invention is to develop a method to produce the halogenated dideoxy sugar derivative as disclosed above, wherein the reaction mechanisms are as follows:

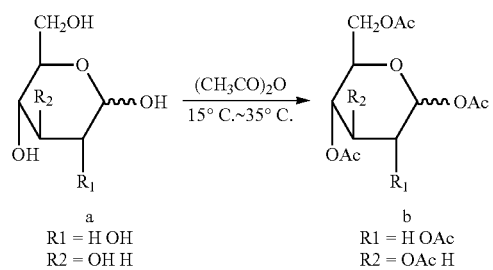

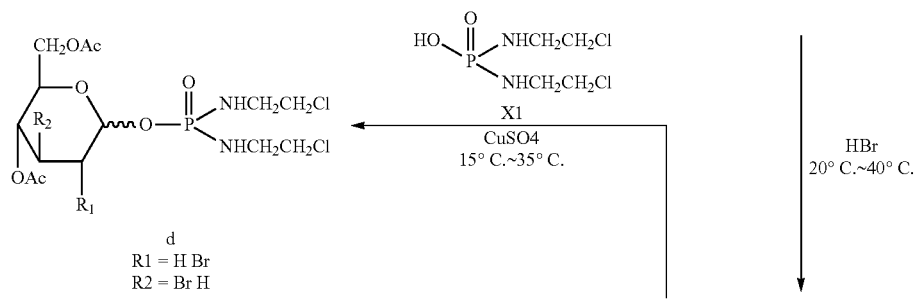

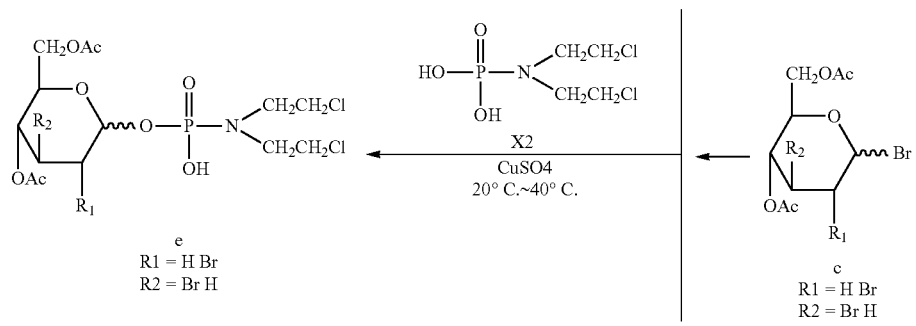

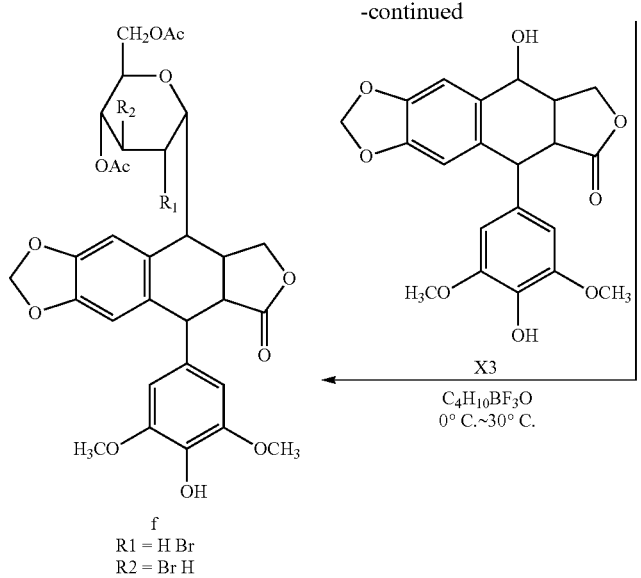

f
R1 = H Br
R2 = Br H

The method comprises the following steps:

(1) Preparing Halogenated Dideoxy Glucose Bromide c

Use 2-deoxy glucose or 3-deoxy glucose a as starting material, and react with acetic anhydride under 15° C.-35° C., and stir the reaction mixture for 2 h-5 h. The molar ratio between the starting material and the acetic anhydride is 1-1.5:15-20. After the reaction, silica gel column chromatography is used to wash the products. The volume of the column is 100 ml. The column capacity is 1%. The flow rate is 1-2 ml/min. The eluant is chosen from chloroform, dichloromethane, dichloroethane, petroleum ether, tetrahydrofuran or toluene. It can also be a mixture of the two or more of the above solvents. The product is then crystallized and re-crystallized using anhydrous chloroform, dichloromethane, ethyl acetate, toluene, ethanol or methanol. Product b is obtained.

The molar ratio between product b and HBr is 1-1.5:3.5-5. The reaction pressure is increased by 0.5-1 kPa. The reaction temperature is 20° C.-45° C. The reaction is stirred for 10 h-18 h. After the reaction, silica gel column chromatography is used to wash the products. The volume of the column is 100 ml. The column capacity is 1%. The flow rate is 1-2 ml/min. The eluant is chosen from chloroform, dichloromethane, dichloroethane, petroleum ether, tetrahydrofuran or toluene. It can also be a mixture of the two or more of the above solvents. α and β two different products are separated due to their different optical nature. The product is then crystallized and re-crystallized using anhydrous chloroform, dichloromethane, ethyl acetate, toluene, ethanol or methanol. Product c is obtained.

(2) The Synthesis Reaction of Halogenated Dideoxy Glucose Bromide and Mustine, Podophyllotoxin.

1) The Synthesis Reaction of Halogenated Dideoxy Glucose Bromide and [N',N'-Di-(2-Chloroethyl)]-Phosphorous Diamine.

Use compound c and compound [N',N'-di-(2-chloroethyl)]-phosphorus diamine as starting material. The molar ratio between compound c and [N',N'-di-(2-chloroethyl)]-phosphorus diamine is 1:1.2-1.5. The solvent is tetrahydrafuran, dichloromethane, chloroform or ethyl acetate. $Ag_2CO_3$ or $CuSO_4$ is used as catalyst, wherein the molar ratio between the catalyst and the compound c is 0.05-0.1:1. The reaction temperature is 15° C.-35° C. The reaction is stirred for 5 h-10 h. After the reaction, silica gel column chromatography is used to wash the products. The volume of the column is 100 ml. The column capacity is 1%. The flow rate is 1-2 ml/min. The eluant is chosen from chloroform, dichloromethane, dichloroethane, petroleum ether, tetrahydrofuran or toluene. It can also be a mixture of the two or more of the above solvents.

α and β two different products are separated due to their different optical nature. The product is then crystallized and re-crystallized using anhydrous chloroform, dichloromethane, ethyl acetate, toluene, ethanol or methanol. Product d is obtained.

2) Synthesis Reaction of Halogenated Dideoxy Glucose Bromide and N-Di-Chloroethyl-Phosphorous Diamine.

Use compound c and compound N-di-chloroethyl-phosphorous diamine as starting material. The molar ratio between compound c and [N',N'-di-(2-chloroethyl)]-phosphorus diamine is 1:1.2-1.5. The solvent is tetrahydrafuran, dichloromethane, chloroform or ethyl acetate. $Ag_2CO_3$ or $CuSO_4$ is used as catalyst, wherein the molar ratio between the catalyst and the compound c is 0.05-0.1:1. The reaction temperature is 20° C.-40° C. The reaction is stirred for 5 h-10 h. After the reaction, silica gel column chromatography is used to wash the products. The volume of the column is 100 ml. The column capacity is 1%. The flow rate is 1-2 ml/min. The eluant is chosen from chloroform, dichloromethane, dichloroethane, petroleum ether, tetrahydrofuran or toluene. It can also be a mixture of the two or more of the above solvents.

α and β two different products are separated due to their different optical nature. The product is then crystallized and re-crystallized using anhydrous chloroform, dichloromethane, ethyl acetate, toluene, ethanol or methanol. Product e is obtained.

3) Synthesis Reaction Between Halogenated Dideoxy Glucose Bromide and 4'-Demethylepipodophyllotoxin Use compound c and 4'-demethylepipodophyllotoxin as starting material. The molar ratio between compound c and 4'-demethylepipodophyllotoxin is 1:1.8-2.2. The solvent is tetrahydrofuran, dichloromethane, chloroform or ethyl acetate. Boron trifluoride ethyl ether is used as catalyst. The molar ratio between catalyst and compound c is 0.1-0.15:1.

Under 0-30° C., the reaction is stirred for 12 h-15 h. After the reaction, silica gel column chromatography is used to wash the products. The volume of the column is 100 ml. The column capacity is 1%. The flow rate is 1-2 ml/min. The eluant is chosen from chloroform, dichloromethane, dichloroethane, petroleum ether, tetrahydrofuran, or toluene. It can also be a mixture of the two or more of the above solvents. The product is then crystallized and recrystallized using anhydrous chloroform, dichloromethane, ethyl acetate, toluene, ethanol, or methanol. Product f is obtained.

Another goal of the current invention is to provide a use of halogenated dideoxy sugar derivative as disclosed above in the production of anti-tumor medicament.

In particular, the current invention discloses the application of compound 1-14 in the treatment of various cancers.

The acute toxicity and anti-cancer effect of the compound are shown as follows:

1. The result of the acute toxicity experiments (LD50) of compound 1-14 (experiments 1-8 are preparation experiments). The results show that compound 1-14 has a relatively low toxicity.

2. In vitro anti-tumor activity experiments

The cytostatic effect of compound 1-14 on human melanoma M 14 cells.

The cytostatic effect of compound 1-14 on human pancreatic cancer cells PC-3.

The cytostatic effect of compound 1-14 on human anaplastic thyroid carcinoma TA-K cells.

The cytostatic effect of compound 1-14 on human nasopharyngeal cancer CNE-2Z cells.

The cytostatic effect of compound 1-14 on human lung cancer A549 cells.

The cytostatic effect of compound 1-14 on human colon cancer HT-29 cells.

The cytostatic effect of compound 1-14 on human liver cancer Bel-7402 cells.

The cytostatic effect of compound 1-14 on human stomach cancer BGC-803 cells.

The cytostatic effect of compound 1-14 on human esophagus cancer CaEs-17 cells:

The cytostatic effect of compound 1-14 on human breast cancer cells MCF-7.

The cytostatic effect of compound 1-14 on human ovarian cancer cells A2780.

The cytostatic effect of compound 1-14 on human bladder cells EJ.

The cytostatic effect of compound 1-14 on human brain glia cells.

The cytostatic effect of compound 1-14 on human leukemia cells K562.

Compound 1-14 has strong cytostatic effect on all of the cancer cells above.

The inhibition effect of compounds 3, 5, 7, 10, 12 and 14 on mouse transplant tumors: Anti-tumor experiments have been conducted on B16 malignant melanoma, AsPc human pancreatic cancer cells, 05-732 human bone tumor, anaplastic thyroid carcinoma TA-K cells, MX-1 human breast cancer cells and MGC human stomach cancer cells. Compound 3, 5, 7, 10, 12 and 14 have significant effect on mouse transplant tumors, especially to malignant melanoma, human pancreatic cancer cells, human bone tumor, anaplastic thyroid carcinoma, human breast cancer cells and human stomach cancer cells.

The current invention uses sugar as starting material to synthesize compound 1-14. Since the sugar rings of all the compounds are acetylated hydrophobic esters, they are very easy to be crystallized. The compounds are chemically and enzymetically stable. They are easy to spread after enter the human body and can be absorbed by cancer cells without consuming any energy. Inside cancer cells, they release the anti-cancer elements, dideoxy sugar, mustine, podophyllotoxin with the help of esterase, acylase and glycosidase and the double anti-tumor effect can be achieved.

The inventor of the current invention has discovered that after the deoxy sugar is acetylated and brominated, the compound is more ready to be absorbed and the anti-tumor effect thereof is significantly better than deoxy sugar. In addition, when the compound is deacetylated, its anti-tumor effect is also significantly improved. However, it is more difficult to be crystallized and therefore acetylated compound is more preferred.

The compound of the current invention can be combined with appropriate excipients and be made into oral medications or non-oral injective agents or external medication. Such as orally administrated pills, capsules, tablets, oral liquids, injections, powder injector, patch or cream.

The compounds of the current invention can be used to treat malignant melanoma, pancreas cancer, anaplastic thyroid carcinoma, metastatic tumor of bone, leukemia, lymphoma, osteoma, chondrosarcoma, prostate cancer, esophagus cancer, stomach cancer, liver cancer, carcinoma of gallbladder, rectum cancer, intestinal cancer, colorectal cancer, lung cancer, prostate cancer, nervous system cancer, breast cancer, ovarian cancer, cervis cancer.

DETAILED DESCRIPTION OF THE EMBODIMENTS

Example 1

Preparation of Compounds 1 and 2

Take 10 g of 2-deoxy glucose and 85 ml acetic anhydride. First add 85 ml acetic anhydride into the reactor and control the temperature at 20° C. Then add 2-dedoxy glucose and the temperature shall not exceed 30° C. Stir the reaction mixture for 3 hours. Use chloroform for extraction and crystallize to obtain 13.8 g pure tetraacetate-2-deoxy glucose.

Take 10 g tetraacetate-2-deoxy glucose, and 0.088 mol HBr gas. First add CH2Cl2 and tetraacetate-2-deoxy glucose into the sealed reactor. After tetraacetate-2-deoxy glucose is completely dissolved under 25° C., add HBr into the mixture and increase the pressure (0.7 kPa) and stir the mixture for 15 hours. After purification and crystallization, 8.3 g tri-acetate-2-deoxy glucose bromide is obtained.

Silica gel chromatography is used to separate $\alpha$, $\beta$ two configurations. Use dichloromethane: methane=80:20 eluent to separate $\alpha$, $\beta$ two configurations. 2.4 g $\alpha$ compound (compound 1) and 3.2 g $\beta$ compound (compound 2) are obtained.

Compound 1: melting point=83° C.-85° C., optical rotation=+5°

Compound 2: melting point=78° C.-80° C., optical rotation=−26°

Element Analysis:

| compound | formular | | C | H | N |
|---|---|---|---|---|---|
| 1 | $C_{10}H_{14}O_5Br_2$ | Test value | 30.45% | 3.52% | |
| | | Caculated value | 31.91% | 3.72% | |
| 2 | $C_{10}H_{14}O_5Br_2$ | Text value | 31.18% | 3.62% | |
| | | Caclulated value | 31.91% | 3.72% | |

Example 2

Preparation of Compounds 3 and 4

Take 10 g of 3-deoxy glucose and 85 ml acetic anhydride. First add 85 ml acetic anhydride into the reactor and control the temperature at 15° C. Then add 3-dedoxy glucose and the temperature shall not exceed 25° C. Stir the reaction mixture for 4 hours. Use chloroform for extraction and crystallize to obtain 11.3 g pure tetraacetate-2-deoxy glucose.

Take 10 g tetraacetate-3-deoxy glucose, and 0.088 mol HBr gas. First add $CH_2Cl_2$ and tetraacetate-3-deoxy glucose into the sealed reactor. After tetraacetate-2-deoxy glucose is completely dissolved under 20° C., add HBr into the mixture and increase the pressure (0.8 kPa) and stir the mixture for 15 hours. After purification and crystallization, 7.8 g tri-acetate-2-deoxy glucose bromide is obtained.

Silica gel chromatography is used to separate α, β two configurations. Use dichloromethane: methane=80:20 eluant to separate α, β configurations. 2.7 g α compound (compound 3) and 2.3 g β compound (compound 4) are obtained.

Compound 3: melting point=88° C.-89° C., optical rotation=−23°

Compound 4: melting point=81° C.-83° C., optical rotation=50°

Element Analysis:

| compound | formular | | C | H | N |
|---|---|---|---|---|---|
| 3 | $C_{10}H_{14}O_5Br_2$ | Test value | 30.67% | 3.89% | |
| | | Calculated value | 31.91% | 3.72% | |
| 4 | $C_{10}H_{14}O_5Br_2$ | Test value | 31.06% | 3.94% | |
| | | Calucated value | 31.91% | 3.72% | |

Example 3

Preparation of Compounds 5, 6

Take 10 g triacetate-2-deoxy glucose bromide and compound X1 14 g. In the reactor, first add tetrahydrofuran, dichlormethane (V/V=1:2), and then add compound X1. After the compound is completely dissolved, CuSO4 is added. Triacetate-2-deoxy glucose bromide is dissolved in dichloromethane and is added dropwise into the reactor. The temperature is controlled at 30° C. The mixture is stirred for 8 hours. After the reaction is over, distilled water is used to wash the compounds for 3-5 times. Methane is used for crystallization and 4.7 g crystals are obtained. Silica gel chromatography is used to separate α, β two configurations. Use acetyl acetate: methane=70:30 eluant to separate α, β two configurations. 1.5 g α compound (compound 5) and 2.1 g β compound (compound 6) are obtained.

Compound 5: melting point=119° C.-120° C., optical rotation=+144°

Compound 6: melting point=108° C.-110° C., optical rotation=−121°

Element Analysis:

| compound | formular | | C | H | N |
|---|---|---|---|---|---|
| 5 | $C_{14}H_{24}O_7N_2PCl_2Br$ | Test value | 32.26% | 4.78% | 5.67% |
| | | Calculated value | 32.62% | 4.66% | 5.44% |
| 6 | $C_{14}H_{24}O_7N_2PCl_2Br$ | Test value | 32.45% | 4.66% | 5.23% |
| | | Calculated value | 32.62% | 4.66% | 5.44% |

Example 4

Preparation of Compounds 7, 8

Take 10 g triacetate-3-deoxy glucose bromide and compound X1 14 g. In the reactor, first add tetrahydrofuran, dichlormethane (V/V=1:2), and then add compound X1. After the compound is completely dissolved, CuSO4 is added. Triacetate-3-deoxy glucose bromide is dissolved in dichloromethane and is added dropwise into the reactor. The temperature is controlled at 18° C. The mixture is stirred for 8 hours. After the reaction is over, distilled water is used to wash the compounds for 3-5 times. Methane is used for crystallization and 3.8 g crystals are obtained. Silica gel chromatography is used to separate α, β two configurations. Use acetyl acetate: methane=75:25 eluant to separate α, β two configurations. 1.9 g α compound (compound 5) and 1.2 g β compound (compound 6) are obtained.

Compound 7: melting point=123° C.-126° C., optical rotation=+106°

Compound 8: melting point=112° C.-114° C., optical rotation=−101°

Element Analysis:

| Compound | Formular | | C | H | N |
|---|---|---|---|---|---|
| 7 | $C_{14}H_{24}O_7N_2PCl_2Br$ | Test value | 32.99% | 4.89% | 5.49% |
| | | Calcucalted value | 32.62% | 4.66% | 5.44% |
| 8 | $C_{14}H_{24}O_7N_2PCl_2Br$ | Test Value | 32.21% | 4.92% | 5.65% |
| | | Calculated Value | 32.62% | 4.66% | 5.44% |

Example 5

Preparation of Compounds 9, 10

Take 10 g triacetate-2-deoxy glucose bromide and compound X2 15 g. In the reactor, first add triethylamine, dichlormethane (V/V=1:5), and then add compound X2. After the compound is completely dissolved, CuSO4 is added. Triacetate-2-deoxy glucose bromide is dissolved in dichloromethane and is added dropwise into the reactor. The temperature is controlled at 20° C. The mixture is stirred for 8 hours. After the reaction is over, distilled water is used to wash the compounds for 3-5 times. Methane is used for crystallization and 5.6 g crystals are obtained. Silica gel chromatography is used to separate α, β two configurations. Use dichloromethane: methane=70:30 eluant to separate α, β two configurations. 3.5 g α compound (compound 9) and 1.4 g β compound (compound 10) are obtained.

Compound 9: melting point=116° C.-118° C., optical rotation=+58°

Compound 10: melting point=104° C.-106° C., optical rotation=−78°

Element Analysis:

| Compound | Formular | | C | H | N |
|---|---|---|---|---|---|
| 9 | $C_{14}H_{22}O_8NPCl_2Br$ | Test Value | 25.47% | 4.67% | 2.92% |
| | | Calculated value | 25.70% | 4.71% | 3.00% |

-continued

| Compound | Formular | | C | H | N |
|---|---|---|---|---|---|
| 10 | $C_{14}H_{22}O_8NPCl_2Br$ | Test Value | 25.36% | 4.57% | 3.12% |
| | | Calculated value | 25.70% | 4.71% | 3.00% |

Example 6

Preparation of Compounds 11, 12

Take 10 g triacetate-3-deoxy glucose bromide and compound X2 15 g. In the reactor, first add triethylamine, dichlormethane (V/V=1:5), and then add compound X2. After the compound is completely dissolved, CuSO4 is added. Triacetate-3-deoxy glucose bromide is dissolved in dichloromethane and is added dropwise into the reactor. The temperature is controlled at 24° C. The mixture is stirred for 9 hours. After the reaction is over, distilled water is used to wash the compounds for 3-5 times. Methane is used for crystallization and 4.6 g crystals are obtained. Silica gel chromatography is used to separate α, β two configurations. Use dichloromethane: methane=75:25 eluant to separate α, β two configurations. 1.8 g α compound (compound 9) and 2.2 g β compound (compound 10) are obtained.

Compound 11: melting point=117° C.-119° C., optical rotation=−5°

Compound 12: melting point=106° C.-109° C., optical rotation=−128°

Element Analysis:

| Compound | Formular | | C | H | N |
|---|---|---|---|---|---|
| 11 | $C_{14}H_{22}O_8NPCl_2Br$ | Test Value | 25.12% | 4.83% | 2.88% |
| | | Calculated value | 25.70% | 4.71% | 3.00% |
| 12 | $C_{14}H_{22}O_8NPCl_2Br$ | Test Value | 25.82% | 4.66% | 2.93% |
| | | Calculated value | 25.70% | 4.71% | 3.00% |

Example 7

Preparation of Compound 13

Take 10 g triacetate-2-deoxy glucose bromide and compound X3 18 g. In the reactor, first add dichlormethane, and then add compound X3. After the compound is completely dissolved, Ag2CO3 is added. Triacetate-2-deoxy glucose bromide is dissolved in dichloromethane and is added dropwise into the reactor. The temperature is controlled at 25° C. The mixture is stirred for 8 hours. After the reaction is over, distilled water is used to wash the compounds for 3-5 times. Methane is used for crystallization and 5.5 g crystals are obtained.

Compound 13: melting point=106° C.-108° C., optical rotation=−85°

Element Analysis:

| Compound | Formular | | C | H | N |
|---|---|---|---|---|---|
| 13 | $C_{31}H_{35}O_{12}Br$ | Test Value | 54.65% | 5.06% | |
| | | Calculated value | 54.71% | 5.15% | |

Example 8

Preparation of Compound 14

Take 10 g triacetate-2-deoxy glucose bromide and compound X3 15 g. In the reactor, first add dichlormethane, and then add compound X3. After the compound is completely dissolved, Ag2CO3 is added. Triacetate-2-deoxy glucose bromide is dissolved in dichloromethane and is added dropwise into the reactor. The temperature is controlled at 20° C. The mixture is stirred for 8 hours. After the reaction is over, distilled water is used to wash the compounds for 3-5 times. Methane is used for crystallization and 5.8 g crystals are obtained.

Compound 13: melting point=120° C.-122° C., optical rotation=+57°

Element Analysis:

| Compound | Formular | | C | H | N |
|---|---|---|---|---|---|
| 14 | $C_{31}H_{35}O_{12}Br$ | Test Value | 54.45% | 4.98% | |
| | | Calculated Value | 54.71% | 5.15% | |

Example 9

The Acute Toxicitiy (LD 50) of Compounds 1-14 (Prepared by Examples 1-8)

1) Mouse ig after given the compound: LD50 (mg/kg)

| 1 | 2 | 3 | 4 | 5 | 6 | 7 |
|---|---|---|---|---|---|---|
| 2438.2 | 2359.3 | 2320.5 | 2389.2 | 2120.4 | 2205.8 | 2218.3 |
| 8 | 9 | 10 | 11 | 12 | 13 | 14 |
| 2017.5 | 2139.4 | 2223.7 | 2028.9 | 2101.4 | 1832.7 | 1965.2 |

2) mouse ip after injection: LD50 (mg/kg)

| 1 | 2 | 3 | 4 | 5 | 6 | 7 |
|---|---|---|---|---|---|---|
| 354.3 | 348.2 | 359.3 | 356.2 | 300.6 | 307.1 | 315.6 |
| 8 | 9 | 10 | 11 | 12 | 13 | 14 |
| 301.4 | 307.2 | 315.6 | 322.6 | 306.4 | 298.7 | 300.2 |

3) In vitro anti-tumor activity experiment
method: MTT experiment
SRB assay
time: 72 hours
Result: no effect: $10^{-5}$ mol/L<85%;

Weak effect: $10^{-5}$ mol/L>85% 或 $10^{-6}$ mol/L>50%

Strong effect: $10^{-6}$ mol/L>85% 或 $10^{-7}$ mol/L>50%

Experiment 10

Use of Compounds 1-14 in the Production of Anti-Cancer Medicament

The results of the acute toxicity and anti-tumor effect of compounds 1-14 are as follows:

The tumor inhibition effect of compounds 1-14 on human nasopharyngeal cancer CNE-2Z cells, human lung cancer A549 cells, human colon cancer HT-29 cells, human liver cancer Bel-7402 cells, human rectum cancer cells HCE 8693, human stomach cancer BGC-803 cells, human esophagus cancer CaEs-17 cells, human breast cancer cells MCF-7, human ovarian cancer cells A2780, pancreatic cancer cells PC-3, human bladder cells EJ, human brain glia cells TG-905, human leukemia cells K562, human melanoma M 14 cells, and human anaplastic thyroid carcinoma TA-K cells are as follows:

The cytostatic effect of compound 1-14 on human melanoma M 14 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 72.3 | 10.3 | strong |
| 2 | 100 | 100 | 99.8 | 74.3 | 14.5 | strong |
| 3 | 100 | 100 | 100 | 74.4 | 16.7 | strong |
| 4 | 100 | 100 | 96.7 | 65.3 | 18.9 | strong |
| 5 | 100 | 100 | 98.5 | 70.5 | 14.2 | strong |
| 6 | 100 | 100 | 94.3 | 68.7 | 11.3 | strong |
| 7 | 100 | 100 | 100 | 72.2 | 15.6 | strong |
| 8 | 100 | 100 | 93.2 | 73.3 | 13.4 | strong |
| 9 | 100 | 100 | 96.1 | 68.4 | 15.6 | strong |
| 10 | 100 | 100 | 100 | 59.7 | 13.4 | strong |
| 11 | 100 | 100 | 100 | 76.5 | 23.2 | strong |
| 12 | 100 | 100 | 100 | 74.3 | 12.1 | strong |
| 13 | 100 | 100 | 100 | 72.1 | 13.3 | strong |
| 14 | 100 | 100 | 98.5 | 68.3 | 16.7 | strong |

The cytostatic effect of compound 1-14 on human pancreas cancer PC-3 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 74.6 | 12.5 | strong |
| 2 | 100 | 100 | 99.6 | 73.2 | 13.6 | strong |
| 3 | 100 | 100 | 100 | 70.8 | 14.8 | strong |
| 4 | 100 | 100 | 100 | 69.5 | 14.9 | strong |
| 5 | 100 | 100 | 100 | 73.4 | 14.7 | strong |
| 6 | 100 | 100 | 100 | 69.3 | 12.5 | strong |
| 7 | 100 | 100 | 100 | 70.1 | 13.6 | strong |
| 8 | 100 | 100 | 100 | 72.3 | 13.4 | strong |
| 9 | 100 | 100 | 96.1 | 69.1 | 15.9 | strong |
| 10 | 100 | 100 | 100 | 69.2 | 12.7 | strong |
| 11 | 100 | 100 | 100 | 71.3 | 13.8 | strong |
| 12 | 100 | 100 | 96.5 | 72.3 | 15.8 | strong |
| 13 | 100 | 100 | 100 | 71.4 | 13.7 | strong |
| 14 | 100 | 100 | 98.7 | 65.2 | 15.7 | strong |

The cytostatic effect of compound 1-14 on human anaplastic thyroid carcinoma TA-K cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 64.5 | 15.6 | strong |
| 2 | 100 | 100 | 100 | 72.4 | 17.4 | strong |
| 3 | 100 | 100 | 100 | 71.6 | 15.6 | strong |
| 4 | 100 | 100 | 100 | 69.7 | 16.9 | strong |
| 5 | 100 | 100 | 98.9 | 70.4 | 13.7 | strong |
| 6 | 100 | 100 | 100 | 69.6 | 15.8 | strong |
| 7 | 100 | 100 | 100 | 68.1 | 12.4 | strong |
| 8 | 100 | 100 | 99.2 | 71.9 | 13.4 | strong |
| 9 | 100 | 100 | 100 | 68.2 | 16.2 | strong |
| 10 | 100 | 100 | 100 | 69.2 | 13.4 | strong |
| 11 | 100 | 100 | 100 | 72.3 | 13.5 | strong |
| 12 | 100 | 100 | 97.9 | 74.5 | 14.7 | strong |

-continued

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 13 | 100 | 100 | 100 | 71.4 | 13.6 | strong |
| 14 | 100 | 100 | 100 | 68.3 | 17.2 | strong |

The cytostatic effect of compound 1-14 on human nasopharyngeal cancer CNE-2Z cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 99.8 | 68.9 | 16.5 | strong |
| 2 | 100 | 100 | 100 | 69.4 | 14.8 | strong |
| 3 | 100 | 100 | 100 | 72.5 | 16.6 | strong |
| 4 | 100 | 100 | 100 | 68.3 | 16.8 | strong |
| 5 | 100 | 100 | 100 | 71.7 | 14.0 | strong |
| 6 | 100 | 100 | 100 | 69.6 | 15.7 | strong |
| 7 | 100 | 100 | 100 | 69.2 | 13.4 | strong |
| 8 | 100 | 100 | 98.7 | 68.9 | 15.6 | strong |
| 9 | 100 | 100 | 98.8 | 68.7 | 15.5 | strong |
| 10 | 100 | 100 | 100 | 70.5 | 13.8 | strong |
| 11 | 100 | 100 | 100 | 71.4 | 12.5 | strong |
| 12 | 100 | 100 | 100 | 71.8 | 14.9 | strong |
| 13 | 100 | 100 | 100 | 69.5 | 15.6 | strong |
| 14 | 100 | 100 | 100 | 68.3 | 16.8 | strong |

The cytostatic effect of compound 1-14 on human lung cancer A549 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 69.7 | 13.6 | strong |
| 2 | 100 | 100 | 100 | 70.8 | 13.8 | strong |
| 3 | 100 | 100 | 100 | 70.9 | 15.7 | strong |
| 4 | 100 | 100 | 100 | 69.3 | 16.2 | strong |
| 5 | 100 | 100 | 100 | 72.5 | 14.5 | strong |
| 6 | 100 | 100 | 100 | 69.8 | 15.3 | strong |
| 7 | 100 | 100 | 100 | 69.5 | 14.1 | strong |
| 8 | 100 | 100 | 100 | 72.9 | 13.8 | strong |
| 9 | 100 | 100 | 100 | 71.4 | 15.7 | strong |
| 10 | 100 | 100 | 100 | 69.5 | 14.2 | strong |
| 11 | 100 | 100 | 100 | 68.7 | 13.4 | strong |
| 12 | 100 | 100 | 100 | 70.4 | 14.9 | strong |
| 13 | 100 | 100 | 100 | 69.9 | 15.1 | strong |
| 14 | 100 | 100 | 100 | 68.7 | 15.7 | strong |

The cytostatic effect of compound 1-14 on human colon cancer HT-29 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 68.5 | 15.5 | strong |
| 2 | 100 | 100 | 99.9 | 71.2 | 14.8 | strong |
| 3 | 100 | 100 | 100 | 70.5 | 13.9 | strong |
| 4 | 100 | 100 | 100 | 69.7 | 16.9 | strong |
| 5 | 100 | 100 | 100 | 71.3 | 14.8 | strong |
| 6 | 100 | 100 | 98.7 | 68.8 | 15.8 | strong |
| 7 | 100 | 100 | 99.6 | 69.6 | 14.6 | strong |
| 8 | 100 | 100 | 100 | 71.4 | 15.5 | strong |
| 9 | 100 | 100 | 100 | 71.6 | 15.9 | strong |
| 10 | 100 | 100 | 100 | 68.5 | 14.7 | strong |
| 11 | 100 | 100 | 100 | 68.9 | 14.8 | strong |
| 12 | 100 | 100 | 100 | 71.7 | 14.5 | strong |

-continued

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 13 | 100 | 100 | 98.8 | 68.5 | 15.6 | strong |
| 14 | 100 | 100 | 100 | 68.3 | 14.9 | strong |

The cytostatic effect of compound 1-14 on human liver cancer Bel-7402 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 68.3 | 13.6 | strong |
| 2 | 100 | 100 | 100 | 69.5 | 13.8 | strong |
| 3 | 100 | 100 | 100 | 67.4 | 15.7 | strong |
| 4 | 100 | 100 | 100 | 68.5 | 16.2 | strong |
| 5 | 100 | 100 | 100 | 67.9 | 14.5 | strong |
| 6 | 100 | 100 | 99.6 | 72.2 | 15.3 | strong |
| 7 | 100 | 100 | 100 | 68.5 | 14.1 | strong |
| 8 | 100 | 100 | 100 | 71.4 | 13.8 | strong |
| 9 | 100 | 100 | 98.9 | 68.7 | 15.7 | strong |
| 10 | 100 | 100 | 97.8 | 69.1 | 14.2 | strong |
| 11 | 100 | 100 | 100 | 68.0 | 13.4 | strong |
| 12 | 100 | 100 | 100 | 71.2 | 14.9 | strong |
| 13 | 100 | 100 | 100 | 69.7 | 15.1 | strong |
| 14 | 100 | 100 | 100 | 68.8 | 15.7 | strong |

The cytostatic effect of compound 1-14 on human rectum cancer HCE 8693 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 69.8 | 15.8 | strong |
| 2 | 100 | 100 | 100 | 72.5 | 14.9 | strong |
| 3 | 100 | 100 | 100 | 69.1 | 13.9 | strong |
| 4 | 100 | 100 | 100 | 71.5 | 14.8 | strong |
| 5 | 100 | 100 | 100 | 68.3 | 15.9 | strong |
| 6 | 100 | 100 | 100 | 71.4 | 15.5 | strong |
| 7 | 100 | 100 | 100 | 69.7 | 14.6 | strong |
| 8 | 100 | 100 | 100 | 64.4 | 14.5 | strong |
| 9 | 100 | 100 | 98.9 | 69.2 | 15.4 | strong |
| 10 | 100 | 100 | 97.8 | 70.1 | 13.8 | strong |
| 11 | 100 | 100 | 100 | 68.8 | 13.7 | strong |
| 12 | 100 | 100 | 100 | 70.5 | 14.5 | strong |
| 13 | 100 | 100 | 100 | 68.9 | 13.4 | strong |
| 14 | 100 | 100 | 100 | 72.3 | 15.9 | strong |

The cytostatic effect of compound 1-14 on human stomache cancer BGC-803 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 70.2 | 15.5 | strong |
| 2 | 100 | 100 | 100 | 71.3 | 16.3 | strong |
| 3 | 100 | 100 | 99.6 | 68.2 | 14.8 | strong |
| 4 | 100 | 100 | 100 | 70.5 | 14.1 | strong |
| 5 | 100 | 100 | 100 | 68.9 | 13.6 | strong |
| 6 | 100 | 100 | 98.9 | 68.4 | 15.2 | strong |
| 7 | 100 | 100 | 100 | 66.9 | 14.9 | strong |
| 8 | 100 | 100 | 100 | 65.8 | 13.6 | strong |
| 9 | 100 | 100 | 100 | 68.2 | 12.7 | strong |
| 10 | 100 | 100 | 98.8 | 72.2 | 14.6 | strong |
| 11 | 100 | 100 | 100 | 68.0 | 16.3 | strong |
| 12 | 100 | 100 | 100 | 71.4 | 16.2 | strong |

-continued

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 13 | 100 | 100 | 97.4 | 68.3 | 13.8 | strong |
| 14 | 100 | 100 | 100 | 70.5 | 15.4 | strong |

The cytostatic effect of compound 1-14 on human esophagus cancer CaEs-17 Cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 72.5 | 18.3 | strong |
| 2 | 100 | 100 | 99.1 | 71.4 | 17.2 | strong |
| 3 | 100 | 100 | 98.7 | 69.3 | 18.4 | strong |
| 4 | 100 | 100 | 100 | 70.7 | 15.3 | strong |
| 5 | 100 | 100 | 99.6 | 69.7 | 19.3 | strong |
| 6 | 100 | 100 | 100 | 68.5 | 15.4 | strong |
| 7 | 100 | 100 | 100 | 67.4 | 16.3 | strong |
| 8 | 100 | 100 | 100 | 65.9 | 14.9 | strong |
| 9 | 100 | 100 | 100 | 69.6 | 14.8 | strong |
| 10 | 100 | 100 | 97.9 | 71.4 | 16.2 | strong |
| 11 | 100 | 100 | 100 | 67.8 | 16.9 | strong |
| 12 | 100 | 100 | 100 | 72.5 | 14.5 | strong |
| 13 | 100 | 100 | 100 | 69.5 | 18.6 | strong |
| 14 | 100 | 100 | 100 | 72.7 | 15.8 | strong |

The cytostatic effect of compound 1-14 on human breast cancer MCF-7 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 71.8 | 11.2 | strong |
| 2 | 100 | 100 | 99.8 | 68.8 | 14.7 | strong |
| 3 | 100 | 100 | 100 | 65.3 | 13.6 | strong |
| 4 | 100 | 100 | 100 | 67.2 | 15.3 | strong |
| 5 | 100 | 100 | 100 | 68.6 | 16.8 | strong |
| 6 | 100 | 100 | 100 | 69.6 | 12.8 | strong |
| 7 | 100 | 100 | 100 | 71.3 | 13.6 | strong |
| 8 | 100 | 100 | 100 | 66.8 | 12.6 | strong |
| 9 | 100 | 100 | 99.6 | 65.2 | 15.3 | strong |
| 10 | 100 | 100 | 100 | 68.8 | 14.8 | strong |
| 11 | 100 | 100 | 100 | 69.4 | 12.3 | strong |
| 12 | 100 | 100 | 100 | 70.7 | 14.8 | strong |
| 13 | 100 | 100 | 98.7 | 68.3 | 12.7 | strong |
| 14 | 100 | 100 | 100 | 70.5 | 16.1 | strong |

The cytostatic effect of compound 1-14 on human ovarian cancer A2780 cells:

| Sample No. | concentration | | | | | evaluation |
|---|---|---|---|---|---|---|
| | $10^{-4}$ | $10^{-5}$ | $10^{-6}$ | $10^{-7}$ | $10^{-8}$ | |
| 1 | 100 | 100 | 100 | 71.8 | 16.2 | strong |
| 2 | 100 | 100 | 100 | 72.8 | 17.4 | strong |
| 3 | 100 | 100 | 100 | 74.3 | 13.8 | strong |
| 4 | 100 | 100 | 100 | 70.2 | 15.8 | strong |
| 5 | 100 | 100 | 100 | 69.6 | 16.7 | strong |
| 6 | 100 | 100 | 100 | 71.3 | 13.5 | strong |
| 7 | 100 | 100 | 100 | 72.5 | 14.9 | strong |
| 8 | 100 | 100 | 100 | 69.7 | 14.7 | strong |
| 9 | 100 | 100 | 100 | 68.4 | 16.4 | strong |
| 10 | 100 | 100 | 100 | 69.5 | 15.3 | strong |
| 11 | 100 | 100 | 100 | 69.9 | 16.2 | strong |
| 12 | 100 | 100 | 100 | 72.3 | 15.9 | strong |

-continued

| Sample No. | $10^{-4}$ | $10^{-5}$ | $10^{-6}$ | $10^{-7}$ | $10^{-8}$ | evaluation |
|---|---|---|---|---|---|---|
| 13 | 100 | 100 | 100 | 71.4 | 14.8 | strong |
| 14 | 100 | 100 | 100 | 72.8 | 15.3 | strong |

The cytostatic effect of compound 1-14 on human bladder cancer EJ cells:

| Sample No. | $10^{-4}$ | $10^{-5}$ | $10^{-6}$ | $10^{-7}$ | $10^{-8}$ | evaluation |
|---|---|---|---|---|---|---|
| 1 | 100 | 100 | 99.8 | 68.5 | 15.4 | strong |
| 2 | 100 | 100 | 99.5 | 71.3 | 16.1 | strong |
| 3 | 100 | 100 | 97.3 | 72.0 | 15.3 | strong |
| 4 | 100 | 100 | 100 | 71.5 | 14.9 | strong |
| 5 | 100 | 100 | 98.2 | 69.8 | 18.2 | strong |
| 6 | 100 | 100 | 99.4 | 70.2 | 17.1 | strong |
| 7 | 100 | 100 | 99.5 | 71.7 | 14.6 | strong |
| 8 | 100 | 100 | 99.6 | 68.6 | 14.8 | strong |
| 9 | 100 | 100 | 100 | 69.9 | 15.7 | strong |
| 10 | 100 | 100 | 98.3 | 69.8 | 15.9 | strong |
| 11 | 100 | 100 | 100 | 67.8 | 13.6 | strong |
| 12 | 100 | 100 | 99.6 | 70.5 | 16.9 | strong |
| 13 | 100 | 100 | 100 | 70.7 | 14.5 | strong |
| 14 | 100 | 100 | 97.6 | 68.7 | 15.7 | strong |

The cytostatic effect of compound 1-14 on human brain glia cancer cells:

| Sample No. | $10^{-4}$ | $10^{-5}$ | $10^{-6}$ | $10^{-7}$ | $10^{-8}$ | evaluation |
|---|---|---|---|---|---|---|
| 1 | 100 | 100 | 100 | 69.8 | 16.7 | strong |
| 2 | 100 | 100 | 98.6 | 67.3 | 15.8 | strong |
| 3 | 100 | 100 | 98.9 | 70.5 | 15.6 | strong |
| 4 | 100 | 100 | 96.5 | 67.5 | 14.6 | strong |
| 5 | 100 | 100 | 100 | 68.8 | 17.2 | strong |
| 6 | 100 | 100 | 99.6 | 69.3 | 17.8 | strong |
| 7 | 100 | 100 | 98.7 | 70.5 | 16.3 | strong |
| 8 | 100 | 100 | 98.9 | 69.6 | 15.8 | strong |
| 9 | 100 | 100 | 99.5 | 69.2 | 13.2 | strong |
| 10 | 100 | 100 | 98.7 | 65.4 | 11.3 | strong |
| 11 | 100 | 100 | 100 | 68.2 | 13.5 | strong |
| 12 | 100 | 100 | 100 | 72.8 | 11.7 | strong |
| 13 | 100 | 100 | 100 | 67.7 | 14.2 | strong |
| 14 | 100 | 100 | 100 | 69.7 | 16.7 | strong |

The cytostatic effect of compound 1-14 on human leukemia cells K562:

| Sample No. | $10^{-4}$ | $10^{-5}$ | $10^{-6}$ | $10^{-7}$ | $10^{-8}$ | Evaluation |
|---|---|---|---|---|---|---|
| 1 | 100 | 100 | 100 | 65.9 | 11.4 | strong |
| 2 | 100 | 100 | 100 | 69.7 | 12.3 | strong |
| 3 | 100 | 100 | 100 | 68.3 | 10.6 | strong |
| 4 | 100 | 100 | 100 | 67.9 | 16.6 | strong |
| 5 | 100 | 100 | 100 | 68.9 | 15.6 | strong |
| 6 | 100 | 100 | 100 | 65.2 | 13.2 | strong |
| 7 | 100 | 100 | 100 | 62.5 | 13.4 | strong |
| 8 | 100 | 100 | 100 | 67.8 | 12.8 | strong |
| 9 | 100 | 100 | 100 | 68.2 | 14.5 | strong |
| 10 | 100 | 100 | 100 | 69.3 | 13.6 | strong |
| 11 | 100 | 100 | 100 | 65.7 | 13.9 | strong |
| 12 | 100 | 100 | 100 | 69.8 | 11.2 | strong |
| 13 | 100 | 100 | 100 | 71.3 | 11.5 | strong |
| 14 | 100 | 100 | 100 | 69.2 | 13.9 | strong |

The experiment results above show that the compounds 1-14 of the current invention has strong inhibition effect on human nasopharyngeal cancer CNE-2Z cells, human lung cancer A549 cells, human colon cancer HT-29 cells, human liver cancer Bel-7402 cells, human rectum cancer cells HCE 8693, human stomach cancer BGC-803 cells, human esophagus cancer CaEs-17 cells, human breast cancer cells MCF-7, human ovarian cancer cells A2780, pancreatic cancer cells PC-3, human bladder cells EJ, human brain glia cells TG-905, human leukemia cells K562, human melanoma M 14 cells and human anaplastic thyroid carcinoma TA-K cells. They can be used to prepare anti-tumor medicament and have significant clinic value.

Example 11

Inhibitive Effect of Compounds 3, 5, 7, 10, 12, 14 on the Mouse Transplant Tumor Compound 3, 5, 7, 10, 12, 14 (the preparation of experiment 2, 3, 4, 5, 6, 8) were applied at a concentration of 125 mg/kg. Saline solution was used as a control. The positive group CTX was treated with the compounds at an amount of 0.4 ml/20 g. The compounds were applied once a day for consecutive 7 days. The animals were then compensated. Anti tumor experiments were carried out on B16 malignant melanoma, AsPc human pancreatic cancer cells, 05-732 human bone tumor, anaplastic thyroid carcinoma TA-K cells, MX-1 human breast cancer cells and MGC human stomach cancer cells respectively.

Experiment Results:

B16 Malignant Human Melanoma

| group | Concentration (mg/kg) | weight start | weight end | Weight of tumor | SD | Inhibition of tumor growth (%) |
|---|---|---|---|---|---|---|
| Control groups | 125 | 18.3 | 19.8 | 2.7 | 0.5 | |
| 3 | 125 | 18.2 | 18.3 | 0.6 | 0.4 | 76.8 |
| 5 | 125 | 18.3 | 18.6 | 0.6 | 0.6 | 76.4 |
| 7 | 125 | 18.3 | 18.4 | 0.5 | 0.3 | 80.4% |
| 10 | 125 | 18.3 | 18.3 | 0.7 | 0.5 | 73.1% |
| 12 | 125 | 18.2 | 18.4 | 0.5 | 0.1 | 79.5 |
| 14 | 125 | 18.3 | 18.5 | 0.6 | 0.4 | 76.2 |
| CTX | 45 | 18.3 | 18.6 | 0.7 | 0.2 | 72.5 |

AsPc Human Pancreatic Cancer

| group | Concentration (mg/kg) | weight start | weight end | Weight of tumor | SD | Inhibition of tumor growth |
|---|---|---|---|---|---|---|
| Control groups | 125 | 18.3 | 19.8 | 2.3 | 0.7 | |
| 3 | 125 | 18.2 | 18.3 | 0.5 | 0.3 | 77.3 |
| 5 | 125 | 18.3 | 18.6 | 0.4 | 0.4 | 81.5 |
| 7 | 125 | 18.3 | 18.4 | 0.6 | 0.5 | 73.6 |
| 10 | 125 | 18.3 | 18.3 | 0.5 | 0.2 | 76.9 |

-continued

| group | Concentration (mg/kg) | weight start | weight end | Weight of tumor | SD | Inhibition of tumor growth |
|---|---|---|---|---|---|---|
| 12 | 125 | 18.2 | 18.4 | 0.5 | 0.1 | 77.5 |
| 14 | 125 | 18.3 | 18.5 | 0.3 | 0.2 | 75.2 |
| CTX | 45 | 18.3 | 18.6 | 0.6 | 0.3 | 73.8 |

05-732 Human Osteosarcoma

| group | Concentration (mg/kg) | weight start | weight end | Weight of tumor | SD | Inhibition of tumor growth |
|---|---|---|---|---|---|---|
| Control group | 125 | 18.3 | 19.8 | 2.9 | 0.3 | |
| 3 | 125 | 18.2 | 18.3 | 0.8 | 0.2 | 71.5 |
| 5 | 125 | 18.3 | 18.6 | 0.7 | 0.4 | 74.9 |
| 7 | 125 | 18.3 | 18.4 | 0.5 | 0.3 | 81.3 |
| 10 | 125 | 18.3 | 18.3 | 0.6 | 0.4 | 78.4 |
| 12 | 125 | 18.2 | 18.4 | 0.5 | 0.5 | 75.1 |
| 14 | 125 | 18.3 | 18.5 | 0.8 | 0.1 | 72.3 |
| CTX | 45 | 18.3 | 18.6 | 0.7 | 0.6 | 73.9 |

Human Anaplastic Thyroid Carcinoma Cell TA-K

| group | Concentration (mg/kg) | weight start | weight end | Weight of tumor | SD | Inhibition of tumor growth |
|---|---|---|---|---|---|---|
| Control group | 125 | 18.3 | 19.8 | 2.7 | 0.2 | |
| 3 | 125 | 18.2 | 18.3 | 0.7 | 0.4 | 73.2 |
| 5 | 125 | 18.3 | 18.6 | 0.6 | 0.3 | 76.6 |
| 7 | 125 | 18.3 | 18.4 | 0.4 | 0.5 | 84.2 |
| 10 | 125 | 18.3 | 18.3 | 0.8 | 0.1 | 71.2 |
| 12 | 125 | 18.2 | 18.4 | 0.6 | 0.5 | 75.8 |
| 14 | 125 | 18.3 | 18.5 | 0.6 | 0.7 | 76.2 |
| CTX | 45 | 18.3 | 18.6 | 0.6 | 0.3 | 77.4 |

MX-1 Human Breast Cancer

| group | Concentration (mg/kg) | weight start | weight end | Weight of tumor | SD | Inhibition of tumor growth |
|---|---|---|---|---|---|---|
| Control group | 125 | 18.3 | 19.8 | 2.5 | 0.5 | |
| 3 | 125 | 18.2 | 18.3 | 0.6 | 0.3 | 75.8 |
| 5 | 125 | 18.3 | 18.6 | 0.4 | 0.4 | 83.6 |
| 7 | 125 | 18.3 | 18.4 | 0.5 | 0.5 | 80.8 |
| 10 | 125 | 18.3 | 18.3 | 0.7 | 0.3 | 73.2 |
| 12 | 125 | 18.2 | 18.4 | 0.4 | 0.2 | 82.1 |
| 14 | 125 | 18.3 | 18.5 | 0.6 | 0.4 | 76.3 |
| CTX | 45 | 18.3 | 18.6 | 0.4 | 0.5 | 84.5 |

MGC Human Stomach Cancer

| group | Concentration (mg/kg) | weight start | weight end | Weight of tumor | SD | Inhibition of tumor growth |
|---|---|---|---|---|---|---|
| Control group | 125 | 18.3 | 19.8 | 2.6 | 0.6 | |
| 3 | 125 | 18.2 | 18.3 | 0.7 | 0.3 | 72.5 |
| 5 | 125 | 18.3 | 18.6 | 0.6 | 0.4 | 75.7 |
| 7 | 125 | 18.3 | 18.4 | 0.4 | 0.2 | 83.8 |
| 10 | 125 | 18.3 | 18.3 | 0.6 | 0.5 | 73.2 |
| 12 | 125 | 18.2 | 18.4 | 0.5 | 0.7 | 80.5 |
| 14 | 125 | 18.3 | 18.5 | 0.7 | 0.5 | 71.9 |
| CTX | 45 | 18.3 | 18.6 | 0.5 | 0.6 | 81.2 |

The results above show that compounds 3, 5, 7, 10, 13, 14 (the preparation of experiment 2, 3, 4, 5, 6, 8) have good inhibitive effect against B16 malignant melanoma, AsPc human pancreatic cancer cells, 05-732 human bone tumor, anaplastic thyroid carcinoma TA-K cells, MX-1 human breast cancer cells and MGC human stomach cancer cells under the concentration of 125 mg/kg.

The invention claimed is:

1. A compound, being represented by formula I

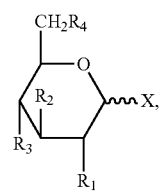

wherein X is

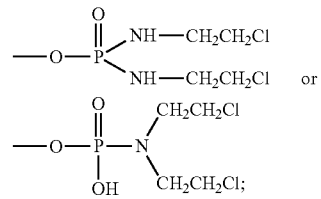

$R_1$ is H and $R_2$ is Br, or $R_1$ is Br and $R_2$ is H; and
$R_3$ and $R_4$ each independently represents OH or OAc.

2. The compound of claim 1,
wherein the compound is

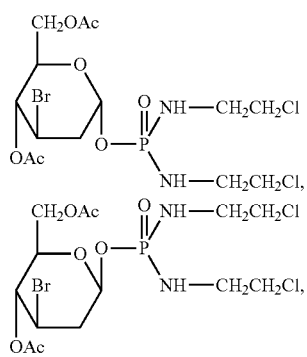

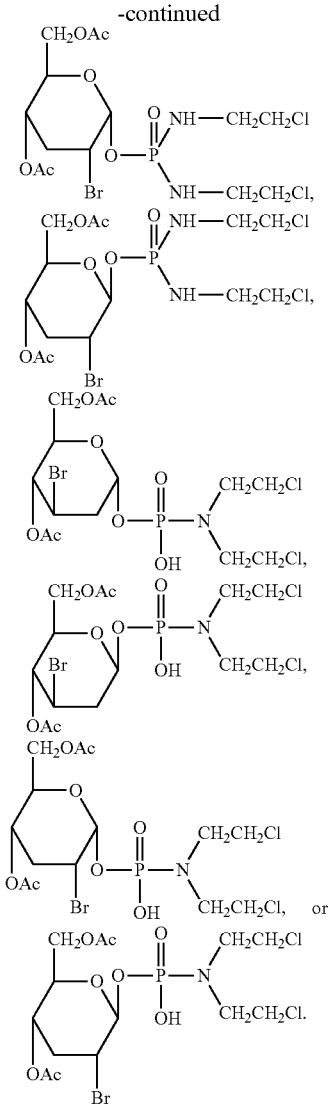

3. An anti-tumor medicament comprising the compound of claim 1.

4. The anti-tumor medicament of claim 3, wherein the anti-tumor medicament is used for treatment of malignant melanoma, pancreas cancer, anaplastic thyroid carcinoma, metastatic tumor of bone, leukemia, lymphoma, osteoma, chondrosarcoma, prostate cancer, esophagus cancer, stomach cancer, liver cancer, carcinoma of gallbladder, rectum cancer, intestinal cancer, colorectal cancer, lung cancer, prostate cancer, nervous system cancer, breast cancer, ovarian cancer, cervis cancer.

5. The anti-tumor medicament of claim 3, further comprising
a pharmaceutically acceptable excipient,
wherein the anti-tumor medicament is made into an oral medication, non-oral injective agent, or external medication with the pharmaceutically acceptable excipient.

6. A method for preparing the compound of claim 1, comprising
reacting 2-deoxy glucose or 3-deoxy glucose with acetic anhydride to yield a tetraacetyl-2-deoxy glucose or a tetraacetyl-3-deoxy glucose, respectively,
reacting the tetraacetyl-2-deoxy glucose or the tetraacetyl 3 deoxy glucose with a hydrogen bromide to yield a 1,2- or 1,3-dibromo-4,6 diacetyl-2,3-dideoxy glucose, and
reacting the 1,2- or 1,3-dibromo-4,6 diacetyl-2,3-dideoxy glucose with an aglycone containing the X to yield the compound of claim 1,
wherein the 2-deoxy glucose or the 3-deoxy glucose reacts with the acetic anhydride at a molar ratio of (1-1.5):(15-20) under a temperature of 15° C. to 35° C. for 2 to 5 hours; and the tetraacetyl-2-deoxy glucose or the tetraacetyl-3-deoxy glucose is recovered by a silica gel column chromatography using an eluant selected from the group consisting of chloroform, dichloromethane, dichloroethane, petroleum ether, tetrahydrofuran, toluene, and a mixture thereof, and is crystallized and recrystallized using a reagent selected from the group consisting of anhydrous chloroform, dichloromethane, ethyl acetate, toluene, ethanol, and methanol; and
the tetraacetyl-2-deoxy glucose or the tetraacetyl-3-deoxy glucose reacts with the hydrogen bromide at a molar ratio of (1-1.5):(3.5-5) at a reaction pressure of 0.5-1 kPa and reaction temperature of 20° C.-45° C.; the 1,2- or 1,3-dibromo-4,6 diacetyl-2,3-dideoxy glucose is recovered by a silica gel column chromatograph using an eluant selected from the group consisting of chloroform, dichloromethane, dichloroethane, petroleum ether, tetrahydrofuran, toluene, and a mixture thereof; the 1,2- or 1,3-dibromo-4,6 diacetyl-2,3-dideoxy glucose is further separated due to optical nature, and crystallized and recrystallized by a reagent selected from the group consisting of anhydrous chloroform, dichloromethane, ethyl acetate, toluene, ethanol, and methanol.

7. The method for preparing the compound according to claim 6, wherein the aglycone is [N',N'-di-(2-chloroethyl)]-phosphorous diamine;
the 1,2- or 1,3-dibromo-4,6 diacetyl-2,3-dideoxy glucose reacts with the [N',N'-di-(2-chloroethyl)]-phosphorous diamine at a molar ratio of 1:(1.2-1.5) in presence of a solvent and a catalyst;
the solvent is selected from the group consisting of tetrahydrafuran, dichloromethane, chloroform, and ethyl acetate;
the catalyst is $Ag_2CO_3$ or $CuSO_4$, and a molar ratio between the catalyst and the 1,2- or 1,3-dibromo-4,6 diacetyl-2,3-dideoxy glucose is (0.05-0.1):1;
the reaction temperature is 15° C.-35° C.;
the reaction is stirred for 5 to 10 hours;
compound is recovered by a silica gel column chromatography using an eluant selected from the group consisting of chloroform, dichloromethane, dichloroethane, petroleum ether, tetrahydrofuran, toluene, and a mixture thereof; and
the compound is separated due to optical nature, and crystallized and recrystallized using a reagent selected from the group consisting of anhydrous chloroform, dichloromethane, ethyl acetate, toluene, ethanol, and methanol.

8. The method for preparing the compound according to claim 6, wherein the aglycone is N-di-chloroethyl-phosphorous diamine;
the 1,2- or 1,3-dibromo-4,6 diacetyl-2,3-dideoxy glucose reacts with the N-di-chloroethyl-phosphorous diamine at a molar ratio of 1: (1.2-1.5) in presence of a solvent and a catalyst;
the solvent is selected from the group consisting of tetrahydrafuran, dichloromethane, chloroform, and ethyl acetate;
the catalyst is $Ag_2CO_3$ or $CuSO_4$, and a molar ratio between the catalyst and the 1,2 or 1,3-dibromo-4,6 diacetyl-2,3-dideoxy glucose is (0.05-0.1):1;

a reaction temperature is 20° C. to 40° C.;
a reaction mixture is stirred for 5 to 10 hours;
the compound is recovered by a silica gel column chromatography using an eluant selected from the group consisting of chloroform, dichloromethane, dichloroethane, petroleum ether, tetrahydrofuran, toluene, and a mixture thereof; and
the compound is separated due to optical nature, and crystallized and recrystallized using a reagent selected from the group consisting of anhydrous chloroform, dichloromethane, ethyl acetate, toluene, ethanol, and methanol.

9. A compound being represented by formula I

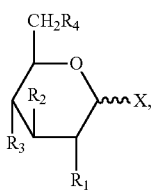

wherein X is a bromide;
$R_1$ is Br and $R_2$ is H; and
$R_3$ and $R_4$ each independently represents OH or OAc.

10. The compound according to claim 9, wherein X is Br, and the compound is

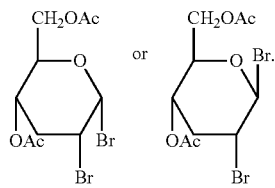

11. An anti-tumor medicament comprising the compound of claim 9.

12. The anti-tumor medicament of claim 11, wherein the anti-tumor medicament is used for treatment of malignant melanoma, pancreas cancer, anaplastic thyroid carcinoma, metastatic tumor of bone, leukemia, lymphoma, osteoma, chondrosarcoma, prostate cancer, esophagus cancer, stomach cancer, liver cancer, carcinoma of gallbladder, rectum cancer, intestinal cancer, colorectal cancer, lung cancer, prostate cancer, nervous system cancer, breast cancer, ovarian cancer, cervis cancer.

13. The anti-tumor medicament of claim 11, further comprising
a pharmaceutically acceptable excipient,
wherein the anti-tumor medicament is made into an oral medication, non-oral injective agent, or external medication with the pharmaceutically acceptable excipient.

14. A method for making the compound of claim 9, comprising
reacting 2-deoxy glucose or 3-deoxy glucose with acetic anhydride to yield a tetraacetyl-2-deoxy glucose or a tetraacetyl-3-deoxy glucose, respectively,
reacting the tetraacetyl-2-deoxy glucose or the tetraacetyl-3-deoxy glucose with a hydrogen bromide to yield the compound of claim 9,
wherein the 2-deoxy glucose or the 3-deoxy glucose reacts with the acetic anhydride at a molar ratio of (1-1.5):(15-20) under a temperature of 15° C. to 35° C. for 2 to 5 hours; and the tetraacetyl-2-deoxy glucose or the tetraacetyl-3-deoxy glucose is recovered by a silica gel column chromatography using an eluant selected from the group consisting of chloroform, dichloromethane, dichloroethane, petroleum ether, tetrahydrofuran, toluene, and a mixture thereof, and crystallized and recrystallized using a reagent selected from the group consisting of anhydrous chloroform, dichloromethane, ethyl acetate, toluene, ethanol, and methanol; and
the tetraacetyl-2-deoxy glucose or the tetraacetyl-3-deoxy glucose reacts with the hydrogen bromide at a molar ratio of (1-1.5):(3.5-5) at a reaction pressure of 0.5 to 1 kPa and a reaction temperature of 20° C. to 45° C.; the compound of claim 9 is recovered by a silica gel column chromatograph using an eluant selected from the group consisting of chloroform, dichloromethane, dichloroethane, petroleum ether, tetrahydrofuran, toluene, and a mixture thereof; the compound is separated due to optical nature, and crystallized and recrystallized by a reagent selected from the group consisting of anhydrous chloroform, dichloromethane, ethyl acetate, toluene, ethanol, and methanol.

15. A compound, being represented by formula I

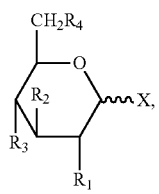

wherein X is

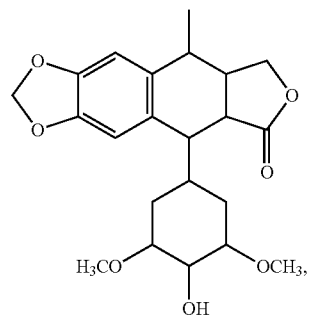

$R_1$ is H and $R_2$ is Br, or $R_1$ is Br and $R_2$ is H; and
$R_3$ and $R_4$ each independently represents OH or OAc.

16. The compound according to claim 15, wherein the compound is

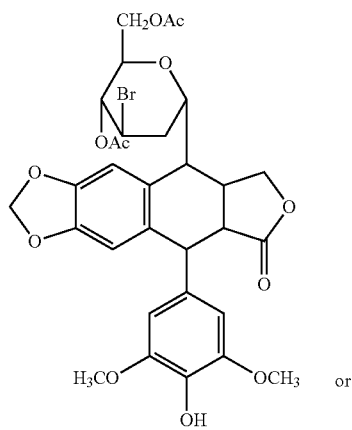 or

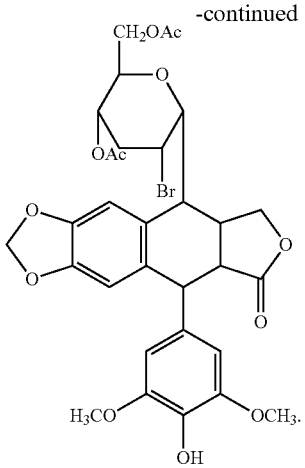

17. An anti-tumor medicament comprising the compound of claim 15.

18. The anti-tumor medicament of claim 17, wherein the anti-tumor medicament is used for treatment of malignant melanoma, pancreas cancer, anaplastic thyroid carcinoma, metastatic tumor of bone, leukemia, lymphoma, osteoma, chondrosarcoma, prostate cancer, esophagus cancer, stomach cancer, liver cancer, carcinoma of gallbladder, rectum cancer, intestinal cancer, colorectal cancer, lung cancer, prostate cancer, nervous system cancer, breast cancer, ovarian cancer, cervis cancer.

19. The anti-tumor medicament of claim 17, further comprising
    a pharmaceutically acceptable excipient,
        wherein the anti-tumor medicament is made into an oral medication, non-oral injective agent, or external medication with the pharmaceutically acceptable excipient.

20. A method for making the compound of claim 15, comprising
    reacting 2-deoxy glucose or 3-deoxy glucose with acetic anhydride to yield a tetraacetyl-2-deoxy glucose or a tetraacetyl-3-deoxy glucose,
    reacting the tetraacetyl-2-deoxy glucose or the tetraacetyl-3-deoxy glucose with a hydrogen bromide to yield a 1,2- or 1,3-dibromo-4,6 diacetyl-2,3-dideoxy glucose, and
    reacting the 1,2- or 1,3-dibromo-4,6 diacetyl-2,3-dideoxy glucose with 4'-demethylepipodophyllotoxin to yield the compound of claim 15, wherein the 2-deoxy glucose or the 3-deoxy glucose reacts with the acetic anhydride at a molar ratio of (1-1.5):(15-20) under a temperature of 15° C. to 35° C. for 2 to 5 hours; and the tetraacetyl-2-deoxy glucose or the tetraacetyl-3-deoxy glucose is recovered by a silica gel column chromatography using an eluant selected from the group consisting of chloroform, dichloromethane, dichloroethane, petroleum ether, tetrahydrofuran, toluene, and a mixture thereof, and crystallized and recrystallized using a reagent selected from the group consisting of anhydrous chloroform, dichloromethane, ethyl acetate, toluene, ethanol, and methanol;

the tetraacetyl-2-deoxy glucose or the tetraacetyl-3-deoxy glucose reacts with the hydrogen bromide at a molar ratio of (1-1.5):(3.5-5) at a reaction pressure of 0.5 to 1 kPa and a reaction temperature of 20° C. to 45° C.; the compound is recovered by a silica gel column chromatograph using an eluant selected from the group consisting of chloroform, dichloromethane, dichloroethane, petroleum ether, tetrahydrofuran, toluene, and a mixture thereof; the compound is separated due to optical nature, and crystallized and recrystallized by a reagent selected from the group consisting of anhydrous chloroform, dichloromethane, ethyl acetate, toluene, ethanol, and methanol; and the 1,2- or 1,3-dibromo-4,6 diacetyl-2,3-dideoxy glucose reacts with the 4'-demethylepipodophyllotoxin at a molar ratio of 1:(1.8-2.2) in presence of a solvent and a catalyst; the solvent is tetrahydrofuran, dichloromethane, chloroform, or ethyl acetate; the catalyst is boron trifluoride ethyl ether; a molar ratio between the catalyst and the 1,2- or 1,3-dibromo-4,6 diacetyl-2,3-dideoxy glucose is (0.1-0.15):1; a reaction temperature is 0 to 30° C., and reaction mixture is stirred for 12 to 15 hours; the compound of claim 15 is recovered by a silica gel column chromatography using an eluant selected from the group consisting of chloroform, dichloromethane, dichloroethane, petroleum ether, tetrahydrofuran, toluene, and a mixture thereof; and the compound is crystallized and recrystallized using a reagent selected from the group consisting of anhydrous chloroform, dichloromethane, ethyl acetate, toluene, ethanol, and methanol.

* * * * *